United States Patent [19]

Knierzinger et al.

[11] Patent Number: 5,110,955
[45] Date of Patent: May 5, 1992

[54] TOCOPHEROL SYNTHESIS: CHROMANE CYCLIZATION AND CATALYSIS

[75] Inventors: Andreas Knierzinger; Michelangelo Scalone, both of Birsfelden, Switzerland

[73] Assignee: Hoffmann-La Roche Inc., Nutley, N.J.

[21] Appl. No.: 505,873

[22] Filed: Apr. 5, 1990

[30] Foreign Application Priority Data

Apr. 14, 1989 [CH] Switzerland ............... 1411/89
Jan. 30, 1990 [CH] Switzerland ............... 288/90

[51] Int. Cl.$^5$ ............................. C07D 311/72
[52] U.S. Cl. ................................ 549/411; 549/410
[58] Field of Search ......................... 549/411, 410

[56] References Cited

U.S. PATENT DOCUMENTS

| | | | |
|---|---|---|---|
| 4,344,886 | 8/1990 | Horner et al. | 549/408 |
| 4,652,657 | 3/1987 | Broger et al. | 548/402 |

FOREIGN PATENT DOCUMENTS

| | | |
|---|---|---|
| 036160 | 9/1981 | European Pat. Off. |
| 158875 | 10/1985 | European Pat. Off. |
| 0218970 | 4/1987 | European Pat. Off. |
| 245959 | 11/1987 | European Pat. Off. |

OTHER PUBLICATIONS

Helvetica Chimica Acta, 46(3), 963 (1963).
Organic Reaction, vol. 19, Ch. 1, J. Wiley & Sons, NY, pp. 44-47 (1972).
J. Org. Chem. 41(22), 3505 (1976).
Tetrahedron Letters, 4, 321 (1979).
J. Org. Chem., 45 (12), 2526 (1980).
Aspects of Homogeneous Catalysis, vol. 4, pp. 145-202, D. Reidel Publishing, Dordrecht, Holland (1981).
Inorg. Chem., 21(6), 2134 (1982).
J. Am. Chem. Soc., 107(7), 2033 (1985).
Helvetica Chimica Acta, 71, 897 (1988).
Helvetica Chimica Acta, 61, 837 (1978).

Primary Examiner—Nicky Chan
Attorney, Agent, or Firm—George M. Gould; George W. Johnston; Alan P. Kass

[57] ABSTRACT

The invention relates to a process for the manufacture of vinylchromanes. This process is concerned with the manufacture of the compounds having the formula

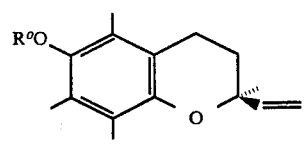

I wherein $R^o$ is hydrogen or a cleavable protecting group, and comprises cyclizing a compound having the formula

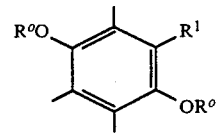

II wherein $R^o$ is defined above and $R^1$ is $$-CH_2-CH_2-C(W)(CH_3)-CH=CH_2 \text{ or}$$

$$-CH_2-CH_2C(CH_3)=CH-CH_2-W$$

where W is a leaving group, by means of a chiral transition metal-diphosphine complex.

The compounds of formula I are useful intermediates, e.g. in the manufacture of (R,R,R)-α-tocopherol.

19 Claims, No Drawings

TOCOPHEROL SYNTHESIS: CHROMANE CYCLIZATION AND CATALYSIS

BACKGROUND OF THE INVENTION

Field of the Invention

The invention relates to vinylchromane compounds and a process for the manufacture thereof.

SUMMARY OF THE INVENTION

The invention relates to vinylchromane compounds and a process for the manufacture thereof. The process is concerned with the manufacture of compounds having the formula

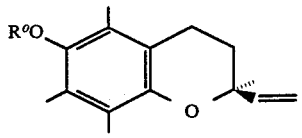

I where $R^o$ is hydrogen or a cleavable protecting group, and comprises cyclizing a compound having the formula

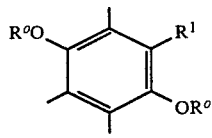

II where $R^o$ is defined above and $R^1$ represents

—$CH_2$—$C(W)(CH_3)$—$CH$=$CH_2$ or

—$CH_2$—$CH_2$—$C(CH_3)$=$CH$—$CH_2$—W where W is a leaving group,
by means of a chiral transition metal-diphosphine complex.

The two substituents $R^o$ can be the same or different from each other.

W represents an ester grouping, for example, having the formulae

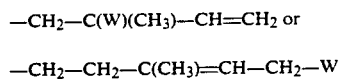

wherein
R′=lower-alkyl, perfluoro-$C_{1-20}$-alkyl, D
R″=lower-alkyl, D, —$CH_2$—D.

D is phenyl which can optionally have in the ortho-, meta-, or paraposition lower-alkyl or lower-alkoxy groups or di-lower-alkylamino groups. The prefered di-lower-alkylamine is dimethylamino.

Alternatively, W can represent a halide or an aryloxy group.

DETAILED DESCRIPTION OF THE PREFERRED EMBODIMENTS

The invention relates to vinylchromane compounds and a process for the manufacture thereof. The process is concerned with the manufacture of compounds having the formula

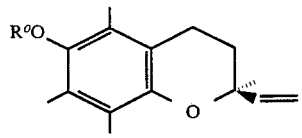

I where $R^o$ is hydrogen or a cleavable protecting group, and comprises cyclizing a compound having the formula

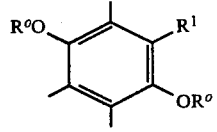

II where $R^o$ is defined above and $R^1$ represents

—$CH_2$—$CH_2$—$C(W)(CH_3)$—$CH$=$CH_2$ or

—$CH_2$—$CH_2$—$C(CH_3)$=$CH$—$CH_2$—W where W is a leaving group,
by means of a chiral transition metal-diphosphine complex.

The two substituents $R^o$ can be the same or different from each other.

W represents an ester grouping, for example, of the formulas

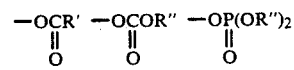

where
R′=lower-alkyl, perfluoro-$C_{1-20}$-alkyl. D
R″=lower-alkyl, D, —$CH_2$—D.

D is phenyl which can optionally have in the ortho-. meta-, or para position lower-alkyl or lower-alkoxy groups or di-lower-alkylamino groups. The prefered di-lower-alkylamine is dimethylamino.

Alternatively, W can represent a halide or an aryloxy group.

The term "lower-alkyl" is in the scope of the present invention straight-chain or branched alkyl groups with 1 to 9 carbon atoms including but not limited to methyl, ethyl, propyl, isopropyl. n-butyl, isobutyl, tert.butyl, pentyl, hexyl, heptyl, octyl, or nonyl.

The term "perfluoro-$C_{1-20}$-alkyl" is in the scope of the present invention not only straight-chain groups, but also branched-chain groups which may be optically active. All hydrogen atoms are not necessarily replaced by fluorine atoms. If all of the hydrogen atoms are not replaced by fluorine atoms, then a terminal hydrogen atom is frequently present.

The term "aryl" used in connection with the compounds of formulae III and IV is in the scope of the present invention not only aromatic hydrocarbons, but also aromatic heterocycles, especially those with 4 to 14 carbon atoms. Preferably, oxygen and nitrogen are the hetero atoms. Furthermore, the rings can be unsubstituted or substituted, preferably with halogen, hydroxy, lower-alkyl, perfluoro-$C_{1-20}$-alkyl, lower alkoxy and formyl. Moreover, an aryl group which is present can be complex-bound to a transition metal such as chromium, iron or nickel.

The letter "D" used hereinafter in connection with the compounds of formulae II, IX and X is in the scope of the present invention phenyl which can optionally have in the ortho-. meta- or para-position lower-alkyl or lower-alkoxy groups or also di-lower-alkylamino, preferably dimethylamino, groups.

The term "halide" is in the scope of the present invention fluoride, chloride, bromide and iodide, with chloride being preferred. The term "halogen" is in the scope of the present invention fluorine, chlorine, bromine and iodine, with fluorine being preferred. The term "aryloxy" is in the scope of the present invention groups where the aryl residue is defined above. The same applies to aroyl. The term "benzyl" signifies CH2-aryl where aryl is defined above. The term "lower-alkoxy" stands for groups in which the alkyl residue has the foregoing significance. The same applies to "lower-alkanoyl". Furthermore, the notation "◂" indicates that the corresponding residue is situated above the plane of the molecule, while the notation " ⦀⦀⦀ " indicates that the corresponding residue is situated below the plane of the molecule.

The transition metal can be a metal of Group 8 of the periodic system, i.e. rhodium, palladium, nickel, platinum, preferably rhodium or palladium.

Examples of suitable complexes are the Rh-complexes set forth in European Patent Publications No. 158 875 and No. 218 970, and are compounds having the formula

[Rh(X)(Y)(L$_{0,1,2}$)]$_{1,2}$   III where

X : halide, BF$_4^-$, PF$_6^-$, ClO$_4^-$, 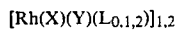 NO$_3^-$, B(C$_6$H$_5$)$_4^-$ or a residue of the formula Z—COO$^-$ which is optionally fixed to a carrier.

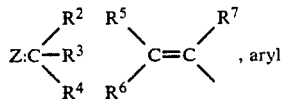

wherein R$^2$, R$^3$, R$^4$ H; halogen; lower alkyl; aryl-lower-alkyl; perfluoro-C$_{1-20}$-alkyl; aryl; OR$^8$;—(CH$_2$)$_n$—COA; AOC—(CF$_2$)$_n$; provided that at least one of R$^2$, R$^3$ and R$^4$ is OR$^8$, aryl or halogen.

R$^5$, R$^6$, R$^7$: H; halogen; lower alkyl; aryl-lower alkyl; perfluoro-C$_{1-20}$-alkyl; aryl; —(CH$_2$)$_n$—COA; AOC—(CF$_2$)$_n$.

T$^8$ : H; lower alkyl; partially or completely halogenated lower alkyl; aryl;aryl-lower-alkyl.

A : —OR'''; NR''''$_2$ in which the substituents R'''' can be the same or different.

R''' : H; lower alkyl; aryl; aryl-lower-alkyl; cation.

R'''': H; lower alkyl; aryl; aryl-lower-alkyl.

n : is an integer from 0 to 20, preferably 0 to 5.

Y : chiral diphosphine ligand.

L : neutral ligand.

The term "neutral ligand" is in the scope of the present invention a readily exchangeable ligand. Examples are: olefins, e.g. ethylene, propylene, cyclo-octene, 1,5-hexadiene, norbornadiene, 1,5-cyclooctadiene and the like, nitriles such as acetonitrile, benzonitrile, or also the solvent which is used. An olefin ligand can be removed, if desired, by previous hydrogenation. Where more than one such ligand is present, these can also be different from one another.

Chiral diphosphine ligands are those diphosphines which are known in connection with asymmetric hydrogenations and which optionally can also be fixed to a carrier. Such ligands are known and are readily accessible to a person skilled in the art. For example, ligands which come into consideration in the scope of the present invention are known from literature references which deal with hydrogenations: Marko, L. et al. Aspects of Homogeneous Catalysis, 4, 145-202 (1981); European Patent Publication No. 245 959; Schmid R. et al., Helv. Chim. Acta, 71, 897-929 (1988). Especially suitable ligands are the chiral diphosphines having the general formulae

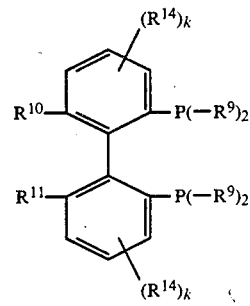

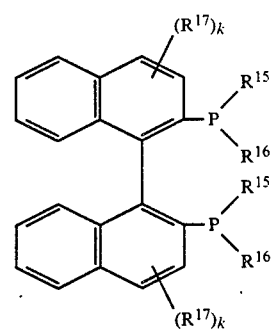

Preferred diphosphine ligands are those of formulae IX and X where:

R$^9$ : D (defined above), cyclohexyl, $^{10}$, R$^{11}$: H; lower-alkyl; lower-alkoxy; di-lower-alkylamino; protected hydroxymethyl. If desired, R$^{10}$ and R$^{11}$ can be different from each other or together can signify the following groups:

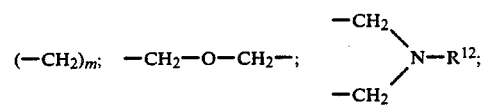

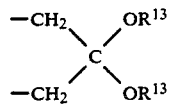

m : is a integer of from 3 to 5,

R$^{12}$: lower alkyl, D, —CH$_2$—D (where D is defined above),

R$^{13}$ : lower alkyl; or both R$^{13}$'s together di- or trimethylene,

R$^{14}$ : —CH$_3$; lower alkoxy; di-lower alkylamino; halogen.

k : is a integer of from 0 to 3

R$^{15}$, R$^{16}$: D (defined above), cyclohexyl,

R$^{17}$ : methyl, ethyl, halogen, —OH; NH$_2$, acetylamino, nitro, —SO$_3$H, preferably in the 5,5'-position.

Examples of preferred diphosphine ligands include:

(6,6'-Dimethylbiphenyl-2,2'-diyl)bis(diphenylphosphine) [BIPHEMP];

6,6'-(dimethylbiphenyl-2,2'-diyl)bis(di-m-toly-phosphine) [mTolBIPHEMP];

6,6'-Dimethylbiphenyl-2,2'-diyl)bis(di-p-tolylphosphine) [PTolBIPHEMP];

2,2'-bis(diphenylphosphino)-1,1'-binaphthyl [BINAP];

2,2'-bis(di-p-tolylphosphino)-1,1'-binaphthyl [PTol-BINAP]; and 2,2'-bis(di-m-tolylphosphino)-1,1'-binaphthyl [mTol-BINAP].

MeOBIPHEP = 6.6'-(dimethoxybiphenyl-2,2'-diyl)-bis-(diphenylphosphine

Preferred rhodium-diphosphine complexes of formula III are those where Z is

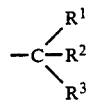

wherein one of R$^1$, R$^2$ and R$^3$ represents fluorine and the remaining two represent halogen, perfluoro-C$_{1-20}$-alkyl or aryl.

Where the ligand X is chiral, this can be present in racemic form [(R):(S)=1:1] or, preferably, in optically active form.

The Rh-complexes of formula III can be prepared for example, in accordance with European Patent Publication No. 158 875 or from the reaction of [(1,5-cyclooctadiene)(X$^1$)Rh] with a diphosphine ligand Y (according to Fryzuk M.D., Inorg. Chem., 21, 2134-2139 (1982) [academic investigation; without information relating to the use of the Products]) and an acid of the formula Z—COOH, in which X$^1$ represents a π-allylic ligand of the type

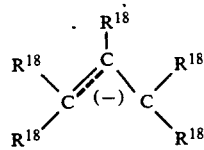

wherein R$^{18}$ signifies hydrogen, aryl, lower alkyl or benzyl and Y and Z as defined above The substituents R$^{18}$ can also be different from one another.

The configuration of the ligand Y determines the configuration of the product I. In order to arrive at the (S)-vinylchromane I (precursor for (R,R,R)-α-tocopherol) in accordance with the invention, the ligand Y is used in the (R)- or (S)-form depending on the nature of the catalyst and on the reaction conditions: a determination of the configuration of the product represented by formula I provides the required information in a simple manner.

Further, complexes of the formula

[Pd(X)(X$^1$)(Y)]  IV wherein X, X$^1$ and Y are defined above, have been found to be suitable.

These latter complexes are well known to those of ordinary skill in the art. See, for example, B. Bosnich et al., J. Am. Chem. Soc., 107, 2033-2045 (1985) "Asymmetric Synthesis. Asymmetric Catalytic Allylation Using Palladium Chiral Phosphine Complexes," from the corresponding diphosphine, a compound [Pd(X)(X$^1$)]$_{1,2}$ and, if desired, a salt having the acid residue X.

The compounds III and IV can be synthesized or can be prepared in situ from the components in the presence of the compound II to be cyclized.

The cyclization in accordance with the invention is conveniently carried out in a temperature range of about −20° C. to about 100° C., especially in a range of about 0° C. and 60° C.

The cyclization is conveniently carried out in a solvent, especially an optionally halogenated aliphatic or aromatic hydrocarbon, e.g. methylene chloride, chloroform or toluene, an ether, e.g. tetrahydrofuran or dioxane, an ester, e.g. ethyl acetate, an alcohol, e.g. methanol, ethanol, tert-butanol, an amide, e.g. dimethylformamide, or a sulphoxide, e.g. dimethyl sulphoxide, in an organic base or in the presence of an organic base, e.g. pyridine, dimethylaminopyridine. In certain cases it is advantageous to convert the compounds II into a salt by reaction with an inorganic base, e.g. sodium hydride, calcium hydride, lithium hydride or potassium hydride, prior to cyclization.

The amount of catalyst is generally from about 0.01 to 10 wt.% (based on the compound II), and is preferably from about 1 to 5 wt.%.

The protecting group R$^o$, preferably from a group selected from lower-alkyl, alkanoyl, aroyl or optionally substituted benzyl, is cleaved off after the cyclization in accordance with the invention either acidically, basically or by hydrogenolysis in a manner well known in the art.

The process provided by the present invention permits the manufacture in good chemical and optical yield ("enantiomeric excess") of optically active chromane ring building blocks for the production of (R,R,R)-α-tocopherol, intermediates which, moreover, already have the configuration of (R,R,R)-α-tocopherol at the C$_2$-atom.

Compound I obtained in accordance with the invention is conveniently converted by hydroboration and oxidation into a compound having the formula

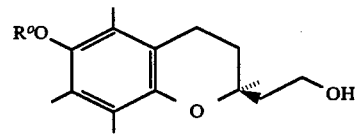

VI wherein R$^o$ is defined above, see, for example, H.C. Brown, J.C. Chen, J. Org. Chem., 46, 3988 (1981) where 3-borabicyclo[3,3,1]nonane is used as the hydroboration agent and hydrogen peroxide is used as the oxidation agent.

Compound VI can be converted into (R,R,R)-1 α-tocopherol in a manner well known in the art, see e.g. N. Cohen et al., J. Org. Chem., 41, 3505, (1976), where the activation of the functional residue of the compound VI and the coupling with the requisite C$_{14}$-side chain derivative is described.

The compounds of formula II can be prepared according to methods well known in the art.

The racemic compounds

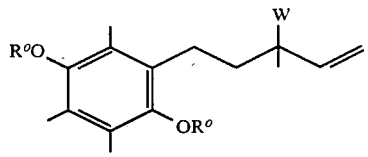

are accessible e.g. from the corresponding substituted chromanes of the formula

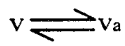

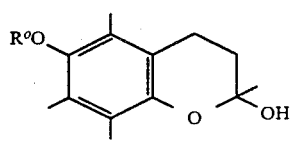

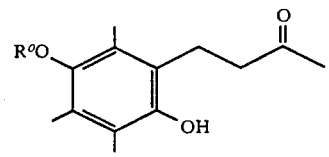

Depending on the conditions, the hemi-acetal V is in equilibrium with the ketone Va. The compounds V are known, see e.g. N. Cohen et al., Helv. Chim. Acta, 61, 837–843 (1978), or can be prepared in analogy to these known methods.

V (or Va) can be converted into IIa according to methods which are well known in the art by, for example, reaction with a vinyl-Grignard compound and subsequent esterification, where it is preferable to first protect the reactive phenolic OH group in the usual manner, e.g. by silylation.

Prochiral compounds of formula IIb and IIc, where $R^o$ and W have been defined above, can also be prepared starting from V, e.g. via allyl rearrangement of IIa in analogy to L.E. Overman and F.M. Knoll, Tetrahedron Letters (1979), 321 et seq.: "Palladium (II)-Catalyzed Rearrangement of Allylic Acetates".

Alternatively, the compounds of formula IIb and IIc are also obtainable from suitably substituted trimethylhydroquinone derivatives by here elongating a suitable, reactive substituent into to the residue $R^1$.

Such reactive trimethylhydroquinone derivatives are, for example,

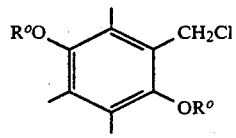

and, respectively,

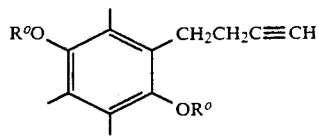

where $R^o$ is defined above.

obtainable therefrom (i.e. from VII) by coupling with a Grignard compound. Both $R^o$'s can be the same or different.

The further conversion of VIII can be carried out according to methods which are known per se to a person skilled in the art, whereby the usual selective methods can be used for the Production of trisubstituted double bonds in the (E)- or (Z)-form.

Compound IIb (W=OH) Protected at the two Phenolic OH groups, where the double bond is Present in the (E)-form, can be prepared e.g. by carbometallation and hydroxymethylation of the triple bond in analogy to E.I. Negishi et al., J. Org. Chem., 45, 2526 (1980) "Conversion of Methyl Ketones into Terminal Acetylenes and (E)-Trisubstituted Olefins of Terpenoid Origin". Compound IIc (W=OH) protected at the two phenolic OH groups, where the double bond is present in the (Z)-form, can be obtained on the other hand by methoxycarbonylation, nucleophilic methylation of the triple bond with copper compounds in analogy to G.H. Posner, Organic Reactions, 19, 45/46 (1972) "α,β-Acetylenic Carbonyl Derivatives" (stereoselective synthesis) and subsequent reduction of the ester group.

The subsequent esterification of the allylic hydroxy group followed by the oxidative cleavage of the protecting groups and reduction of the quinones to the hydroquinones gives, according to methods which are well known to those of ordinary skill in the art, the respective appropriately W- and $R^o$-substituted trimethylhydroquinone derivatives IIb and IIc in pure (E)- and (Z)-forms, respectively.

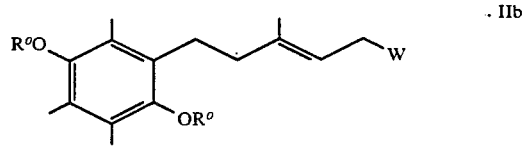

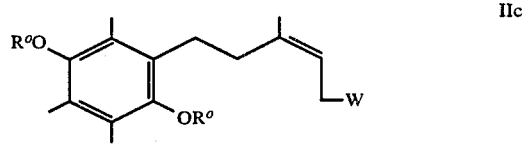

EXAMPLES

The following Examples illustrate the invention and in no manner represent a limitation thereof. In these Examples the abbreviations used have the following significance:

COD=1,5-cyclooctadiene
BINAP=2,2'bis(diphenylphosphino)-1,1'-binaphthyl
BIPHEMP=6,6'-(dimethylbiphenyl-2,2'-diyl)-bis(diphenylphosphine)
mTolBIPHEMP=6,6'-(dimethylbiphenyl-2,2'-diyl)-bis(di-m-tolylphosphine)

pTolBIPHEMP = 6,6'-(dimethylbiphenyl-2,2'-diyl)-bis(di-p-tolylphosphine)
mTolBINAP = 2,2'-bis(di-m-tolylphosphino)-1,1'-binaphthyl
pTolBINAP = 2,2'-bis(di-p-tolylphosphino)-1,1'-binaphthyl
MeOBIPHEP = 6.6'-(dimethoxybiphenyl-2,2'-diyl)-bis(diphenylphosphine)
9-BBN = 9-borabicyclo[3.3.1]nonane The enantiomeric composition (optical purity) of the cyclization products is based on the specific optical rotation (589 nm. 20°) of the pure vinylchromanes of formula I having the (S)-configuration:

$R^o = H$, $[\alpha] = -89.0°$ (c = 0.5, chloroform)
$R^o = $ methyl, $[\alpha] = -77.5°$ (c = 0.3, chloroform)
$R^o = $ acetyl, $[\alpha] = -79.5°$ (c = 1.0, octane)[1]
$R^o = $ benzyl, $[\alpha] = -58.7°$ (c = 1.0, chloroform)

[1] H.J. Mayer, P. Schudel, R. Rüegg and O. Isler, Helv. Chim. Acta, 46, 963 (1963), the process is commercially unattractive; the chromane building block is prepared according to a non-catalytic procedure; racemate resolution thus leads to a minimum loss of 50%; the optically active resolving agent is expensive and must accordingly be recycled.

A₁ Racemic DIOLS type IIa

EXAMPLE 1

A solution of 10.0 g (32.0 mmol) of rac. 6-benzyloxy-2-hydroxy-2,5,7,8-tetramethylchromane in THF (50 ml) was treated dropwise at −20° C. with 68.4 ml (88.4 mmol) of a solution of 1.3M vinylmagnesium bromide. After completion of the addition the reaction mixture was warmed to room temperature and stirred further for 2 hours. Thereafter, the reaction mixture was washed at 0° C. with a saturated ammonium chloride solution (70 ml). The white precipitate (inorganic salts) was filtered off under suction, washed with ether and discarded. The aqueous phase was extracted with ether, the combined organic Phases were dried and evaporated. Crystallization of the oily residue from ether/hexane gave 9.30 g of 2-[(R,S)-3-hydroxy-3-methyl-4-pentenyl]-3,5,6-trimethyl-4-benzyloxyphenol with a melting point of 96°-99° C.

Further diols were prepared in an analogous manner:
From rac. 6-acetoxy-2-hydroxy-2,5,7,8-tetramethyl-chromane: 4-hydroxy-3-(3-hydroxy-3-methyl-4-pentenyl)-2,5,6-trimethylphenyl acetate (m.P. 104°-105° C.).
From rac. 6-methoxy-2-hydroxy-2,5,7,8-tetramethyl-chromane: 2-[(R,S)-3-hydroxy-3-methyl-4-pentenyl]-4-methoxy-3,5,6-trimethylphenol (colourless oil; MS: 264 (M+), 246 (−H₂O), 231 (−H₂O, −CH₃), 217, 179, 178; IR: 3387, 2932, 2829, 1454, 1409, 1251, 1084).

A₂ Racemic ESTER

EXAMPLE 2

A solution of 10.0 g (29.4 mmol) of 2-[(R.S)-3-hydroxy-3-methyl-4-pentenyl]-3,5,6-trimethyl-4-benzyloxyphenol in THF (75 ml) was treated dropwise at 0° C. with 39.5 ml (63.3 mmol) of a solution of 1.6M butyllithium in hexane and stirred for 1 hour. Thereafter, there was added dropwise while stirring at 0° C. firstly a solution of 5.0 ml (39.1 mmol) of trimethyl-chlorosilane in THF (8 ml) and, after 1.5 hours, a solution of 3.0 ml (31.7 mmol) of acetic anhydride in THF (7.5 ml). After 2 hours the reaction mixture was washed at 0° C. with a saturated ammonium chloride solution (50 ml), the aqueous phase was extracted with ether and discarded. The combined organic phases were dried and the oil remaining after removal of the solvent was purified on silica gel (eluent: ether/ hexane 1:3). A solution of 8.4 g (18.5 mmol) of the isolated, colourless oil in THF (52 ml) was treated at 0° C. with a solution of 6.2 g (19.7 mmol) of tetrabutylammonium fluoride in THF (21 ml). After stirring at 0° C. for 1 hour the reaction mixture was washed with a saturated ammonium chloride solution (35 ml). The aqueous phase was extracted with ether, the combined organic phases were dried and evaporated. After filtration of the residue on silica gel, crystallization from ether/n-hexane gave 5.86 g of (R,S)-1-[3-benzyloxy-6-hydroxy-2,4,5-trimethyl-phenethyl]-1-methylallyl acetate with a melting Point of 62°-63.5° C.

Further esters were Prepared in an analogous manner:

From 2-[(R,S)-3-hydroxy-3-methyl-4-pentenyl]-3,5,6-trimethyl-4-benzyloxyphenol:
(R,S)-1-[3-Benzyloxy-6-hydroxy-2,4,5-trimethyl-phenetyl]-1-methylallyl butyrate (m.p. 78°-79° C.).
(R,S)-1-[3-Benzyloxy-6-hydroxy-2,4,5-trimethylphene-thyl]-1-methylallyl methylcarbonate (m.P. 59.5°-61° C.).
(R.S)-1-[3-Benzyloxy-6-hydroxy-2,4,5-trimethylphene-thyl]-1-methylallyl tert-butylcarbonate (m.p. 72°-73° C.).

From 2-[(R,S)-3-hydroxy-3-methyl-4-pentenyl]-4-methoxy-3,5,6-trimethylphenol:
rac-1-(2-Hydroxy-5-methoxy-3,4,6-trimethylphene-thyl)-1-methylallyl acetate (colourless oil; IR: 3474, 1736, 1252).
rac-1-(2-Hydroxy-5-methoxy-3,4,6-trimethylphene-thyl)-1-methylallyl methylcarbonate (m.P. 62.5°-63° C).
rac-1-(2-Hydroxy-5-methoxy-3,4,6-trimethylphene-thyl)-1-methylallyl benzylcarbonate (colourless oil; IR: 3512, 1743, 1265).
rac-1-(2-Hydroxy-5-methoxy-3,4,6-trimethylphene-thyl)-1-methylallyl tert-butylcarbonate (colourless oil; IR: 3508, 1739, 1285, 1252).

From 4-hydroxy-3-(3-hydroxy-3-methyl-4-pentenyl)-2,5,6-trimethylphenyl acetate:
rac-1-(3-Acetoxy-6-hydroxy-2,4,5-trimethylphenethyl)-1-methylallyl methylcarbonate (m.p. 114°-116° C).

B. CYCLIZATIONS

EXAMPLE 3 a) SUBSTRATE type IIa : (R,S)-1-[3-Benzyloxy-6-hydroxy-2,4,5-trimethylphenethyl]-1-methylallyl acetate Experiment 1

6.8 mg (0.0105 mmol) of [Rh(CF₃COO)(COD)]₂ as the Rh Precursor. 13.1 mg (0.021 mmol) of (S)-BINAP as the chiral diphosphine ligand and 6 ml of toluene were placed in a 25 ml Schlenk tube in a Dry Box (O₂ content <1 ppm). After opening the Dry Box closure the solution was stirred for 30 min., 400 mg (1.05 mmol) of (R,S)-1-[3-benzyloxy-6-hydroxy-2,4,5-trimethyl-phenethyl]-1-methylallyl acetate were then added as the substrate and the yellow-orange reaction solution was stirred at room temperature for 2 hours. Thereafter, the reaction solution was stirred for 30 min. without a protecting gas, evaporated and the red, oily crude product was chromatographed on silica gel (eluent: hexane/ether 3:1). After evaporating the eluate which was uniform according to thin-layer chromatography and drying the residue there was obtained 316 mg of pure (S)-6-(benzyloxy)-3,4-dihydro-2,5,7,8-tetramethyl-2- vinyl-2H-1-benzopyran as a colourless oil which solidifies upon standing. Optical Purity: 44.8%, [α]= −26.3°.

Enantiomerically-pure (S)-6-(benzyloxy)-3,4-dihydro-2,5,7,8-tetramethyl-2-vinyl-2H-1-benzopyran was obtained by a single crystallization:

1.30 g of (S)-6-(benzyloxy)-3,4-dihydro-2,5,7,8-tetramethyl-2-vinyl-2H-1-benzopyran (o.p. 46.8%) were dissolved at room temperature in 6 ml of hexane and 1 ml of ether and left to crystallize at 5° for 70 h. After filtration there was obtained 0.378 g of optically pure (S)-6-(benzyloxy)-3,4-dihydro-2,5,7,8-tetramethyl-2-vinyl-2H-1-benzopyran. M.P. 63°–66°.

Experiment 2

The cyclization of 400 mg of (R,S)-1-[3-benzyloxy-6-hydroxy-2,4,5-trimethylphenethyl]-1-methylallyl acetate in the presence of 9.8 mg of [Rh(COD)$_2$]$^+$PF$_6$$^-$ as the Rh precursor and 26.2 mg of (S)-BINAP as the diphosphine ligand was carried out in an analogous manner to Experiment 1. After 16 hours at 60° the mixture was worked-up in a analogous manner to Experiment 1, yielding 162 mg of pure (S)-6-(benzyloxy)-3,4-dihydro-2,5,7,8-tetramethyl-2-vinyl-2H-1-benzopyran. Optical purity 10.6%, [α]= −6.2°.

Experiment 3

The cyclization of 400 mg of (R,S)-1-[3-benzyloxy-6-hydroxy-2,4,5-trimethylphenethyl]-1-methylallyl acetate was carried out at 0° C. in an analogous manner to Experiment 1. After 16 hours the mixture was worked-up in a analogous manner to Experiment 1, yielding 224 mg of pure (S)-6-(benzyloxy)-3,4-dihydro-2,5,7,8-tetramethyl-2-vinyl-2H-1-benzopyran. Optical purity 36.8%, [α]= −21.6°.

Experiment 4

The cyclization of 400 mg of (R,S)-1-[3-benzyloxy-6-hydroxy-2,4,5-trimethylphenethyl]-1-methylallyl acetate in the presence of 12.4 mg of (S)-BIPHEMP as the chiral diphosphine ligand was carried out in an analogous manner to Experiment 1. After 2 hours the mixture is worked-up analogously to Experiment 1, yielding 321 mg of pure (S)-6-(benzyloxy)-3,4-dihydro-2,5,7,8-tetramethyl-2-vinyl-2H-1-benzopyran. Optical purity 42.1%, [α]= −24.2°.

Experiment 4a

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 20.9 mg of (S)-mTolBINAP as the chiral diphosphine ligand was carried out in an analogous manner to Experiment 1. After 2 hours the mixture is worked-up analogous manner to Experiment 1, yielding 885 mg of pure (S)-6-(benzyloxy)-3,4-dihydro-2,5,7,8-tetramethyl-2-vinyl-2H-1-benzopyran. Optical purity 42.9%, [α]= −25.2°.

Experiment 4b

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 20.9 mg of (S)-pTolBINAP as the chiral diphosphine ligand was carried out in an analogous manner to Experiment 1. After 2 hours the mixture was worked-up in an analogous manner to Experiment 1, yielding 881 mg of pure (S)-6-(benzyloxy)-3,4-dihydro-2,5,7,8-tetramethyl-2-vinyl-2H-1-benzopyran. Optical purity 34.8%, [α]= −20.4°.

Experiment 4c

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 18.9 mg of (S)-mTolBIPHEMP as the chiral disphosphine ligand was carried out in an analogous manner to Experiment 1. After 2 hours the mixture was worked-up in an analogous manner to Experiment 1, yielding 888 mg of pure (S)-6-(benzyloxy)-3,4-dihydro-2,5,7,8-tetramethyl-2-vinyl-2H-1-benzopyran. Optical purity 55.0%, [α]= −32.3°.

Experiment 4d

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 18.9 mg of (S)-mTolBIPHEMP as the chiral diphosphine ligand was carried out at 0° C. in an analogous manner to Experiment 1. After 3 hours the mixture was worked-up in an analogous manner to Experiment 1, yielding 870 mg of pure (S)-6-(benzyloxy)-3,4-dihydro-2,5,7,8-tetramethyl-2-vinyl-2H-1-benzopyran. Optical purity 56.6%, [α]= −33.2°.

Experiment 4e

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 18.9 mg of (S)-pTolBIPHEMP as the chiral diphosphine ligand was carried out in an analogous manner to Experiment 1. After 2 hours the mixture was worked-up in an analogous manner to Experiment 1, yielding 882 mg of pure (S)-6-(benzyloxy)-3,4-dihydro-2,5,7,8-tetramethyl-2-vinyl-2H-1-benzopyran. Optical purity 28.6%, [α]= −16.8°.

Experiment 4f

The cyclization of 1.0 g of (R,S)-1-[3-benzyloxy-6-hydroxy-2,4,5-trimethylphenethyl]-1-methylallyl acetate in the presence of 9.1 mg of [Rh(CF$_3$CO$_2$)(COD)]$_2$ and of 18.1 mg of (S)-MeOBIPHEP as the chiral diphosphine ligand was carried out in an analogous manner to Experiment 1. After 2 hours the mixture was worked-up analogously to Experiment 1, yielding 876 mg of pure (S)-6-(benzyloxy)-3,4-dihydro-2,5,7,8-tetramethyl-2-vinyl-2H-1-benzopyran. Optical purity 35.6%, [α]= −20.9°.

Experiment 5

5.2 mg (0.0105 mmol) of [RhCl(COD)]$_2$ as the Rh precursor, 13.1 mg (0.021 mmol) of (S)-BINAP as the chiral diphosphine ligand and 6 ml of toluene were placed in a 25 ml glass autoclave in a Dry Box (O$_2$ content <1 ppm). After pressurization with 15 bar of hydrogen the autoclave was shaken at room temperature for 2 hours. After releasing the gas the dark red catalyst solution was placed in a 25 ml Schlenk tube. 400 mg (1.05 mmol) of (R,S)-1-[3-benzyloxy-6- -hydroxy-2,4,5-trimethylphenethyl]-1-methylallyl acetate (1.05 mmol) was added and the yellow-orange reaction solution was stirred at 80° C. for 18 hours. The mixture was worked-up in an analogous manner to Experiment 1, yielding 239 mg of pure (S)-6-(benzyloxy)-3,4-dihydro-2,5,7,8-tetramethyl-2-vinyl-2H-1-benzopyran. Optical purity: 45.1%, [α]= −26.5°.

b) SUBSTRATE type IIa : (R,S)-1-[3-Benzyloxy-6-hydroxy-2,4,5-trimethylphenethyl]-1-methylallyl methylcarbonate

Experiment 6

The cyclization of 3.34 g of (R,S)-1-[3-benzyloxy-6-hydroxy-2,4,5-trimethylphenethyl]-1-methylallyl methylcarbonate in the presence of 27.2 mg of [Rh(CF$_3$COO)—(COD)]$_2$ as the Rh precursor and 57.6 mg of (S)-BINAP as the diphosphine ligand was carried out in an analogous manner to Experiment 1. After 2 hours at room temperature the mixture was worked-up in an analogous manner to Experiment 1, yielding 2.07 g of pure (S)-6-(benzyloxy)-3,4-dihydro- ,5,7,8-tetramethyl-2-vinyl-2H-1-benzopyran. Optical purity 42.7%, [α]=−25.1°.

Experiment 6a

The cyclization of 1.0 g of (R,S)-1-[3-benzyloxy-6-hydroxy-2,4,5-trimethylphenethyl]-1-methylallyl methylcarbonate in the presence of 9.1 mg of [Rh(CF$_3$COO)(COD)]$_2$ and 18.9 mg of (S)-mTolBIPHEMP as the diphosphine ligand was carried out in an analogous manner to Experiment 1. After 2 hours at room temperature the mixture was worked-up in an analogous manner to Experiment 1, there was obtained 792 mg of pure (S)-6-(benzyloxy)-3,4-dihydro-2,5,7,8-tetramethyl-2-vinyl-2H-1-benzopyran. Optical purity 43.4%, [α]=−25.5°.

Experiment 6b

The cyclization of 1.0 g of (R,S)-1-[3-benzyloxy-6-hydroxy-2,4,5-trimethylphenethyl]-1-methylallyl methylcarbonate in the presence of 9.1 mg of [Rh(CF$_3$COO)(COD)]$_2$ and 18.9 mg of (S)-pTolBIPHEMP as the diphosphine ligand was carried out in an analogous manner to Experiment 1. After 2 hours at room temperature the mixture is worked-up in an analogous manner to Experiment 1, yielding 716 mg of pure (S)-6-(benzyloxy)-3,4-dihydro-2,5,7,8-tetramethyl-2-vinyl-2H-1-benzopyran. Optical purity 39.5%, [α]=−23.2°.

Experiment 6c

The cyclization of 1.0 g of (R,S)-1-[3-benzyloxy-6-hydroxy-2,4,5-trimethylphenethyl]-1-methylallyl methylcarbonate in the presence of 9.1 mg of [Rh(CF$_3$COO)(COD)]$_2$ and 18.1 mg of (S)-MeOBIPHEP as the disphosphine ligand was carried out in an analogous manner to Experiment 1. After 2 hours at room temperature the mixture was worked-up in an analogous manner to Experiment 1, yielding 502 mg of pure (S)-6-(benzyloxy)-3,4-dihydro-5,7,8-tetramethyl-2-vinyl-2H-1-benzopyran. Optical Purity 40.2%. [α]=−23.6°.

Experiment 7

34.1 mg (0.084 mmol) of [Rh(COD)$_2$]$^+$ BF$_4^-$ and 57.4 mg (0.092 mmol) of (S)-BINAP in 32 ml of toluene were placed in a flask in a Dry Box (O$_2$ content <1 ppm). After stirring for 2 hours 31.4 mg (0.088 mmol) of tetrabutylammonium trifluoroacetate and 4 ml of toluene were added and the suspension was stirred until a red-orange solution was obtained (22–24 h). Thereafter, a solution of 3.35 g of (R,S)-1-[3-benzyloxy-6-hydroxy-2,4,5-trimethyl-phenethyl]-1-methylallyl methylcarbonate in 12 ml of toluene was added and the orange solution was stirred for 2 hours. Thereafter, the mixture was worked-up in an analogous manner to Experiment 1, yielding 2.06 g of pure (S)-6-(benzyloxy)-3,4-dihydro-2,5,7,8-tetramethyl-2-vinyl-2H-1-benzopyran. Optical Purity: 37.1%, [α]=−21.8°.

Experiment 8

7.2 mg (0.0288 mmol) of [Rh(2-methylallyl)(COD)] and 19.4 mg (0.031 mmol) of (S)-BINAP in 17 ml of toluene were placed in a flask in a Dry Box (O$_2$ content <1 ppm). After stirring for 30 min. 3.2 mg (0.0281 mmol) of trifluoroacetic acid was added as a solution in 1 ml of toluene and, after a further 30 min., 1.12 g of (R,S)-1-[3-benzyloxy-6-hydroxy-2,4,5-trimethylphenethyl]-1-methylallyl methylcarbonate was added. After 3 hours the mixture was worked-up analogously to Experiment 1, yielding 0.70 g of pure (S)-6-(benzyloxy)-3,4-dihydro-2,5,7,8-tetramethyl-2-vinyl-2H-1-benzopyran. Optical purity: 40.4%, [α]=−23.8°.

Experiment 9

The cyclization of 3.35 g (8.4 mmol) of (R,S)-1-[3-benzyloxy-6-hydroxy-2,4,5-trimethylphenethyl]-1-methylallyl methylcarbonate in the presence of 8.5 mg (0.021 mmol) of [Rh(COD)$_2$]$^+$BF$_4$ and 7.8 mg (0.022 mmol) of tetrabutylammonium trifluoroacetate was carried out in an analogous manner to Experiment 7. After 5.5 hours the mixture was worked-up in an analogous manner to Experiment 1, yielding 1.94 g of pure (S)-6-(benzyloxy)-3,4-dihydro-2,5,7,8-tetramethyl-2-vinyl-2H-1-benzopyran. Optical purity: 36.6%, [α]=−21.5°.

Experiment 10

A solution of 3.4 mg (0.0052 mmol) of [Rh(CF$_3$COO)(COD)]$_2$ and 7.2 mg of (S)-BINAP in 6 ml of toluene was treated, after pre-hydrogenation, with 0.42 g of (R,S)-1-[3-benzyloxy-6-hydroxy-2,4,5-trimethylphenethyl]-1-methylallyl methylcarbonate in an analogous manner to Experiment 5. After 2 hours the mixture is worked-up in an analogous manner to Experiment 1, yielding 0.33 g of pure (S)-6-(benzyloxy)-3,4-dihydro-2,5,7,8-tetramethyl-2-vinyl-2H-1-benzopyran. Optical purity: 37.4%, [α]=−22.0°.

Experiment 11

The cyclization of 418 mg of (R,S)-1-[3-benzyloxy-6-hydroxy-2,4,5-trimethylphenethyl]-1-methylallyl methylcarbonate in the presence of 6.8 mg of [Rh(CF$_3$COO)(COD)]$_2$ and 13.1 mg of (S)-BINAP in 6 ml of methylene chloride was carried out in an analogous manner to Experiment 1. After 1.5 hours the mixture was worked-up in an analogous manner to Experiment 1, yielding 250 mg of pure (S)-6-(benzyloxy)-3,4-dihydro-2,5,7,8-tetramethyl-2-vinyl-2H-1-benzopyran. Optical purity: 38.1%, [α]=−22.4°.

Experiment 12

The cyclization of 418 mg of (R,S)-1-[3-benzyloxy-6-hydroxy-2,4,5-trimethylphenethyl]-1-methylallyl methylcarbonate in the presence of 6.8 mg of [Rh(CF$_3$COO)(COD)]$_2$ and 13.1 mg of (R)-BINAP in 6 ml of tetrahydrofuran was carried out in an analogous manner to Experiment 1. After 1.5 hours the mixture was worked-up in an analogous manner to Experiment 1, yielding 80 mg of pure (S)-6-(benzyloxy)-3,4-dihydro-2,5,7,8-tetramethyl-2-vinyl-2H-1-benzopyran. Optical purity: 19.9%, [α]=−11.7°.

Experiment 13

The cyclization of 418 mg of (R,S)-1-[3-benzyloxy-6-hydroxy-2,4,5-trimethylphenethyl]-1-methylallyl methylcarbonate in the presence of 6.8 mg of [Rh(CF$_3$COO)(COD)]$_2$ and 104.8 mg of (S)-BINAP in 6 ml of toluene was carried out in an analogous manner to Experiment 1. After 6.5 hours the mixture was worked-up analogously to Experiment 1, yielding 227 mg of pure (S)-6-(benzyloxy)-3,4-dihydro-2,5,7,8-tetramethyl-2-vinyl-2H-1-benzopyran. Optical purity: 46.0%, [α] = −27.0°.

Experiment 14

The cyclization of 1.11 g (2.9 mmol) of (R,S)-1-[3-benzyloxy-6-hydroxy-2,4,5-trimethylphenethyl]-1-methylallyl methylcarbonate in the presence of 7.1 mg (0.014 mmol) of [RhCl(COD)]$_2$ and 19.5 mg (0.030 mmol) of (S)-BINAP was carried out in an analogous manner to Experiment 1. After 24 hours the mixture was worked-up analogously to Experiment 1, yielding 0.685 g of pure (S)-6-(benzyloxy)-3,4-dihydro-2,5,7,8-tetramethyl-2-vinyl-2H-1-benzopyran. Optical purity: 41.4%, [α] = −24.3°.

Experiment 15

The cyclization of 1.11 g (2.9 mmol) of (R,S)-1-[3-benzyloxy-6-hydroxy-2,4,5-trimethylphenethyl]-1-methylallyl methylcarbonate in the presence of 13.2 mg (0.028 mmol) of [Rh(COD)$_2$]$^+$ PF$_6^-$ and 36 7 mg (0.059 mmol) of (S)-BINAP was carried out in an analogous manner to Experiment 1. After 64 hours the mixture was worked-up in an analogous manner to Experiment 1, yielding 0.374 g of pure (S)-6-(benzyloxy)-3,4-dihydro-2,5,7,8-tetramethyl-2-vinyl-2H-1-benzopyran. Optical purity: 24.4%, [α] = −14.4°.

Experiment 16

The cyclization of 418 mg (1.05 mmol) of (R,S)-1-[3-benzyloxy-6-hydroxy-2,4,5-trimethylphenethyl]-1-methylallyl methylcarbonate in the presence of 9.9 mg (0.021 mmol) of [Rh(COD)$_2$]$^+$ PF$_6^-$, 14 5 mg (0.023 mmol) of (S)-BINAP and 6.3 mg (0.024 mmol) of tetraethylammonium acetate tetrahydrate in 9 ml of toluene was carried out in an analogous manner to Experiment 7. After 6 hours the mixture was worked-up analogously to Experiment 1, yielding 192 mg of pure (S)-6-(benzyloxy)-3,4-dihydro-2,5,7,8-tetramethyl-2-vinyl-2H-1-benzopyran. Optical purity: 37.4%, [α] = −22.0°.

Experiment 17

The cyclization of 1.12 g (2.80 mmol) of (R,S)-1-[3-benzyloxy-6-hydroxy-2,4,5-trimethylphenethyl]-1-methylallyl methylcarbonate in the presence of 7.2 mg (0.0288 mmol) of [Rh(2-methylallyl)(COD)], 19.4 mg (0.031 mmol) of (S)-BINAP and 1.68 mg (0.028 mmol) of acetic acid in 17 ml of toluene was carried out in an analogous manner to Experiment 8. After 24 hours the mixture was worked-up in an analogous manner to Experiment 1, yielding 0.36 g of pure (S)-6-(benzyloxy)-3,4-dihydro-2,5,7,8-tetramethyl-2-vinyl-2H-1-benzopyran. Optical purity: 35.4%, [α] = −20.8°.

Experiment 18

The cyclization of 3.35 g of (R,S)-1-[3-benzyloxy-6-hydroxy-2,4,5-trimethylphenethyl]-1-methylallyl methylcarbonate in the presence of 34.0 mg of [Rh(COD)$_2$]$^+$ PF$_6^-$ as the Rh precursor, 51.0 mg of (S)-BIPHEMP as the diphosphine ligand and 31.3 mg of tetrabutylammonium trifluoroacetate was carried out in an analogous manner to Experiment 7. After 2 hours at room temperature the mixture was worked-up in an analogous manner to Experiment 1, yielding 2.35 g of (S)-6-(benzyloxy)-3,4-dihydro-2,5,7,8-tetramethyl-2-vinyl-2H-1-benzopyran. Optical purity 28.3%, [α] = −16.6°.

Experiment 19

The cyclization of 3.35 g of (R,S)-1-[3-benzyloxy-6-hydroxy-2,4,5-trimethylphenethyl]-1-methylallyl methylcarbonate in the presence of 27.3 mg of [Rh(CF$_3$COO)(COD)]$_2$ as the Rh precursor and 57.5 mg of (S)-BINAP as the diphosphine ligand was carried out at 0° C. in an analogous manner to Experiment 1. After 24 hours the mixture was worked-up in an analogous manner to Experiment 1, yielding 1.93 g of (S)-6-(benzyloxy)-3,4-dihydro-2,5,7,8-tetramethyl-2-vinyl-2H-1-benzopyran. Optical purity 61.8%, [α] = −36.3°.

Experiment 20

The cyclization of 3.35 g of (R,S)-1-[3-benzyloxy-6-hydroxy-2,4,5-trimethylphenethyl]-1-methylallyl methylcarbonate in the presence of 39.2 mg of [Rh(COD)$_2$]$^+$ PF$_6^-$ as the Rh precursor, 57.5 mg of (S)-BINAP as the diphosphine ligand and 48.0 mg of tetrabutylammonium trifluoroacetate was carried out at 0° C. in an analogous manner to Experiment 7. After 24 hours the mixture was worked-up in an analogous manner to Experiment 1, yielding 1.72 g of (S)-6-(benzyloxy)-3,4-dihydro-2,5,7,8-tetramethyl-2-vinyl-2H-1-benzopyran. Optical purity 58%, [α] = −33.8°.

Experiment 21

The cyclization of 418 mg of (R,S)-1-[3-benzyloxy-6-hydroxy-2,4,5-trimethylphenethyl]-1-methylallyl methylcarbonate in the presence of 6.8 mg of [Rh(CF$_3$COO)(COD)]$_2$ as the Rh precursor and 11.6 mg of (S)-BIPHEMP as the diphosphine ligand was carried out at 0° C. in an analogous manner to Experiment 1. After 24 hours the mixture was worked-up in an analogous manner to Experiment 1. yielding 160 mg of (S)-6-(benzyloxy)-3,4-dihydro-2,5,7,8-tetramethyl-2-vinyl-2H-1-benzopyran. Optical purity 52%, [α] = −30.5°.

Experiment 22

The cyclization of 3.35 g of (R,S)-1-[3-benzyloxy-6-hydroxy-2,4,5-trimethylphenethyl]-1-methylallyl methylcarbonate in the presence of 27.7 mg of [Rh(CF$_3$COO)(COD)]$_2$ as the Rh Precursor and 57.6 mg of (S)-BINAP as the diphosphine ligand in toluene saturated with water was carried out in an analogous manner to Experiment 1. After 2 hours at room temperature the mixture was worked-up in an analogous manner to Experiment 1, yielding 1.10 g of (S)-6-(benzyloxy)-3,4-dihydro-2,5,7,8-tetramethyl-2-vinyl-2H-1-benzopyran. Optical Purity 73.6%, [α] = −43.2°.

Experiment 23

The cyclization of 1.12 g of (R,S)-1-[3-benzyloxy-6-hydroxy-2,4,5-trimethylphenethyl]-1-methylallyl methylcarbonate in the presence of 6.9 mg of [RhCl(COD)]$_2$ as the Rh precursor and 19.2 mg of (S)-BINAP as the diphosphine ligand was carried out in toluene saturated with water in an analogous manner to Experiment 1. After 24 hours at room temperature the mixture was worked-up in an analogous manner to Experiment 1, yielding 252 mg of (S)-6- -(benzyloxy)-3,4-dihydro-2,5,7,8-tetramethyl-2-vinyl-2H-1- -benzopyran. Optical purity 65.7%, [α]=−38.6°.

Experiment 24

The cyclization of 3.35 g of (R,S)-1-[3-benzyloxy-6-hydroxy-2,4,5-trimethylphenethyl]-1-methylallyl methylcarbonate in the presence of 34.1 mg of [Rh(COD)$_2$]$^+$ BF$_4^-$ as the Rh precursor, 57.4 mg of (S)-BINAP as the diphosphine ligand and 31.3 mg of tetrabutylammonium trifluoroacetate in toluene saturated with water was carried out in an analogous manner to Experiment 7. After 2 hours at room temperature the mixture was worked-up in an analogous manner to Experiment 1, yielding 1.23 g of (S)-6-(benzyloxy)-3,4-dihydro-2,5,7,8-tetramethyl-2-vinyl-2H-1-benzopyran. Optical purity 77.6%, [α]=−45.6°.

Experiment 25

The cyclization of 1.12 g of (R,S)-1-[3-benzyloxy-6-hydroxy-2,4,5-trimethylphenethyl]-1-methylallyl methylcarbonate in the presence of 7.0 mg of Rh(methallyl)(-COD)] as the Rh precursor, 19.2 mg of (S)-BINAP as the diphosphine ligand and 3.2 mg of trifluoroacetic acid in toluene saturated with water was carried out in an analogous manner to Experiment 8. After 3 hours at room temperature the mixture was worked-up in an analogous manner to Experiment 1, yielding 0.35 g of (S)-6-(benzyloxy)-3,4-dihydro-2,5,7,8-tetramethyl-2-vinyl-2H-1- -benzopyran. Optical purity 76.9%, [α]=−45.2°.

Experiment 26

The cyclization of 3.35 g of (R,S)-1-[3-benzyloxy-6-hydroxy-2,4,5-trimethylphenethyl]-1-methylallyl methylcarbonate in the presence of 34.1 mg of [Rh(COD)$_2$]$^+$ BF$_4^-$ as the Rh precursor, 50.8 mg of (S)-BIPHEMP as the diphosphine ligand and 31.3 mg of tetrabutylammonium trifluoroacetate in toluene saturated with water was carried out in an analogous manner to Experiment 7. After 2.4 hours at room temperature the mixture was worked-up in an analogous manner to Experiment 1, yielding 1.40 g of (S)-6-(benzyloxy)-3,4-dihydro-2,5,7,8-tetramethyl-2-vinyl-2H-1-benzopyran. Optical purity 67.9%, [α]=−39.9°.

Further asymmetric cyclizations of various allyl alcohol derivatives of formula II, carried out in an analogous manner as set forth in Experiment 1, are set forth in the Table below.

TABLE

Asymmetrical Cyclization of Various Allyl Alcohol Derivatives

| Exp. No | Substrate type | R$^o$ | W | Vinylchromane I Yield [%] | [α] | O.p. [%] |
|---|---|---|---|---|---|---|
| 1 | IIa | Bz | OAc | 95 | −26.3 | 44.8 |
| 6 | " | " | OCO$_2$—Me | 76 | −25.1 | 42.7 |
| 27 | " | " | OCO$_2$-t-Bu | 81 | −21.0 | 35.7 |
| 28 | " | Me | OAc | 86 | −32.9 | 42.5 |
| 29 | " | " | OCO$_2$—Me | 70 | −37.7 | 48.7 |
| 30 | " | " | OCO$_2$-t-Bu | 74 | −25.1 | 32.5 |
| 31 | " | " | OCO$_2$—Bz | 56 | −27.6 | 35.7 |
| 32 | " | Ac | OCO$_2$—Me | 70 | −31.1 | 39.1 |
| 33 | IIb | Bz | OCO$_2$—Me | 42 | −9.8 | 16.7 |

C. Hydroboration-oxidation of I to VI

EXAMPLE 4

This reaction was carried out with reference to H.C. Brown. J.C. Chen, J. Org. Chem., 46, 3988 (1981).

A solution of 1.22 g (10.0 mmol) of 9-borabicyclo-[3.3.1]nonane in tetrahydrofuran (50 ml) was treated with 2.67 g (8.3 mmol) of (R,S)-6-(benzyloxy)-3,4-dihydro-2,5,7,8-tetramethyl-2-vinyl-2H-1-benzopyran and the mixture was stirred at 50° C. for 2 hours. After cooling the reaction mixture there were added in succession ethanol (15 ml), 6N sodium hydroxide solution (7.5 ml) and 30% hydrogen peroxide (7.5 ml) and the mixture was left to react at 50° C. for 3 hours. After cooling the reaction mixture was saturated with potassium carbonate and extracted with ether. The combined organic extracts were dried and evaporated. The residue was Purified on silica gel (eluent: hexane/ether 1:2) and the pure product was crystallized from ether/hexane yielding 2.57 g (91.1%) of white crystals, m.p.: 67.5–68.5.

D. Preparation of the Prochiral Substrates (type IIb, IIc)

EXAMPLE 5 a) A solution of chloromethyltrimethylhydroquinone dimethyl ether (7.5 g; 32 mmol) in THF (20 ml) was treated dropwise at 0° with a freshly Prepared solution of a Grignard reagent Prepared from 1.9 g of magnesium shavings and 4.91 ml (65 mmol) of propargyl bromide. After the addition of solid sodium iodide (0.42 g) the mixture was warmed to room temperature and stirred overnight. Thereafter, the reaction mixture was diluted with ether and washed with 2N hydrochloric acid. The ethereal solution was deacidified with bicarbonate, dried and freed from solvent. Distillation (0.04 mbar; 140° C.) of the residue gave 7.16 g of 1-(3-butynyl)-3,6-dimethoxy-2,4,5-trimethylbenzene; melting point: 54° C.

b) A suspension of zirconocene dichloride (2.61 g; 8.9 mmol) in 1,2-dichloroethane was treated firstly with trimethylaluminium (10.9 ml; 114 mmol), then with a solution of 1-(3-butynyl)-3,6-dimethoxy-2,4,5-trimethylbenzene (10.6 g; 45.7 mmol) in 1,2-dichloroethane (60 ml). The mixture was heated to 50° C. for 46 hours, thereafter cooled to −40°, diluted with THF (20 ml), treated with 40 ml of a 1.6 molar n-butyllithium solution (in hexane) and finally with 4.37 g of paraformaldehyde. The resulting reaction mixture was stirred at room temperature for 20 hours and subsequently introduced into ice-cold 2N hydrochloric acid solution. The mixture was extracted twice with ether and the combined extracts were washed with water and dried. The oil which remained after removal of the solvent was purified on silica gel (eluent: hexane/ethyl acetate=2.5/1), yielding (E)-5-(2,5-dimethoxy-3,4,6-trimethylphenyl)-3-methyl-2-penten-1-ol as a colourless oil which crystallized slowly at room temperature (m.p.: 46° C.).

c) A solution of 4.17 g (15 mmol) of (E)-5-(2,5-dimethoxy-3,4,6-trimethylphenyl)-3-methyl-2-penten-1-ol in pyridine (10 ml) and acetic anhydride (2 ml) was stirred at room temperature for 5 hours and thereafter poured into ice-cold 2N hydrochloric acid solution. The mixture was extracted with ether. The combined extracts were washed with water, dried and freed from solvent; the residue obtained was purified on silica gel with hexane/ethyl acetate (95:5), yielding 3.8 g of (E)-5-(2,5- dimethoxy-3,4,6-trimethylphenyl)-3-methyl-2-pentenyl acetate as a colourless oil.

d) A solution of 3.83 g (12 mmol) of (E)-5-(2,5-dimethoxy-3,4,6-trimethylphenyl)-3-methyl-2-pentenyl acetate in acetonitrile (50 ml) was treated dropwise at 0° C. with a solution of ceric ammonium nitrate (16.4 g; 30 mmol) in water (50 ml). After completion of the addition the mixture was stirred for a further 20 minutes and diluted with water and chloroform. The organic phase was separated, washed with water, dried and concentrated to a yellow oil, yielding (E)-3-methyl-5-(2,4,5-trimethyl-3,6-dioxo-1,4-cyclohexadien-1-yl)-2-pentenyl acetate (3.27 g).

e) A solution of 3.27 g (11.3 mmol) of (E)-3-methyl-5-(2,4,5-trimethyl-3,6-dioxo-1,4-cyclohexadien-1-yl)-2-pentenyl acetate in 60 ml of THF was treated dropwise with 40 ml of a freshly Prepared 0.5M sodium dithionite solution. After completion of the addition the mixture was diluted with water and extracted with chloroform. The combined extracts were washed with water and freed from solvent. The solid residue was washed with hexane and dried under oil pump vacuum, yielding 2.94 g of (E)-5-(2,5-dihydroxy-3,4,6-trimethylphenyl)-3-methyl-2-pentenyl acetate as a colourless powder; m.p. 94.5°–96° C.

a1) A solution of 1 g (3.6 mmol) of (E)-5-(2,5-dimethoxy-3,4,6-trimethylphenyl)-3-methyl-2-penten-1-ol in pyridine (10 ml) was treated in three portions with a total of 1.08 ml of methyl chloroformate and the resulting mixture was stirred overnight. Thereafter, the mixture was poured on to ice and extracted with ethyl acetate. The extracts were washed with water, dried and concentrated, and the residue was purified on silica gel with hexane/ethyl acetate (9:1), yielding 0.8 g of (E)-5-(3,6-dimethoxy-2,4,5- -trimethylphenyl)-3-methyl-2-pentenyl methylcarbonate as a colourless oil.

b1) A solution of 3.8 g (6.9 mmol) of ceric ammonium nitrate in 15 ml of water was added dropwise to a solution, cooled to 0° C, of 0.93 g (2.8 mmol) of (E)-5-(3,6-dimethoxy-2,4,5-trimethylphenyl)-3-methyl-2-pentenyl methylcarbonate in acetonitrile (15 ml). The mixture was stirred for 15 minutes and thereafter extracted twice with 100 ml of chloroform each time. The combined extracts were washed with water, dried and freed from solvent. The residue was chromatographed on silica gel with hexane/ethyl acetate (9:1), yielding 0.73 g of (E)-3-methyl-5-(2,4,5-trimethyl-3,6-dioxo-1,4-cyclohexadien-1-yl)-2-pentenyl methylcarbonate as a pale yellow oil.

c1) A freshly Prepared 0.5M sodium dithionite solution (7.2 ml) was added dropwise to a solution of (E)-3-methyl-5-(2,4,5-trimethyl-3,6-dioxo-1,4-cyclohexadien-1-yl)-2-pentenyl methylcarbonate (0.73 g; 2.4 mmol) in THF (1 ml). After completion of the addition the mixture was diluted with water and extracted with methylene chloride (2×50 ml). The combined extracts were washed with water, dried and freed from solvent. The beige coloured residue was washed firstly with hexane/methylene chloride (6:1) (7 ml) and then with hexane (7 ml). 0.63 g of (E)-5-(3,6-dihydroxy-2,4,5-trimethylphenyl)-2-pentenyl methylcarbonate was obtained. M.P. 101°–102.5° C.

a2) Benzoyl chloride (1 g; 7.1 mmol) was dissolved in pyridine (10 ml) together with (E)-5-(2,5-dimethoxy-3,4,6-trimethylphenyl)-3-methyl-2-penten-1-ol (1.56 g; 5.6 mmol). After 30 minutes the mixture was poured into water and extracted with ether. The extracts were washed with 1N hydrochloric acid, water, saturated bicarbonate solution and again with water. After removing the solvent in vacuo 2 g of (E)-5-(2,5-dimethoxy-3,4,6-trimethylphenyl)-3-methyl-2-pentenyl benzoate was obtained.

b2) A solution of ceric ammonium nitrate (7.2 g; 13.1 mmol) in water (30 ml) was added dropwise while cooling with ice to a solution of (E)-5-(2,5-dimethoxy-3,4,6-trimethylphenyl)-3-methyl-2-pentenyl benzoate (2 g; 5.2 mmol) in acetonitrile (30 ml). After completion of the addition the mixture was diluted with water and extracted with chloroform. The extracts were washed with water, dried and freed from solvent. The residue crystallizes spontaneously and 1.35 g of (E)-3-methyl-5-(2,4,5-trimethyl-3,6-dioxo-1,4-cyclohexadien-1-yl)-2-pentenyl benzoate was obtained. M.P, 74.5°–75.5° C.

c2) A solution of 1.22 g (3.5 mmol) of (E)-3-methyl-5-(2,4,5-trimethyl-3,6-dioxo-1,4-cyclohexadien-1-yl)-2-pentenyl benzoate in 10 ml of THF was treated dropwise with a solution of 0.9 g of sodium dithionite in 8 ml of water. After 1 hour the mixture was extracted with chloroform (2 x) and the combined extracts were washed three times with water. The residue remaining after removal of the solvent was washed with hexane and dried under vacuum, yielding 1.05 g of colourless (E)-5-(2,5-dihydroxy-3,4,6-trimethylphenyl)-3-methyl-2-pentenyl benzoate. M.P. 112°–114° C.

a3) A solution of 5 g (21.5 mmol) of 1-(3-butynyl)-3,6-dimethoxy-2,4,5-trimethylbenzene in 80 ml of THF was cooled to −78° C. and treated firstly with 13.4 ml of a 1.6M n-butyllithium solution and then with 2.2 g (23.3 mmol) of methyl chloroformate. The mixture was left at −78° C. for 1 hour, then warmed to −20° C., held at this temperature for 2 hours and finally poured into saturated ammonium chloride solution. Extraction with ethyl acetate yielded, after washing the extracts with water and drying over sodium sulphate, a yellow oil which was purified on silica gel (eluent: hexane/ethyl acetate 95:5→90:10). There were obtained 3.6 g of spontaneously crystallizing methyl 5-(2,5-dimethoxy-3,4,6-trimethylphenyl)-2-pentynoate. M.P. 71°–72° C.

b3) A solution of lithium dimethylcuprate (prepared from 0.97 g (5.1 mmol) of copper-(I) iodide and 6.4 ml of a 1.6M ethereal methyllithium solution) in ether (30 ml) was cooled to −78° C. and treated dropwise with a solution of methyl 5-(2,5-dimethoxy-3,4,6-trimethylphenyl)-2-pentynoate (1 g; 3.4 mmol) in THF (10 ml). The mixture was stirred at −78° C. for 90 minutes, treated with 0.5 ml of methanol, warmed to room temperature and treated with saturated ammonium chloride solution. The mixture was extracted twice with ether and the combined extracts were washed with water and dried. The remaining residue was purified on silica gel with hexane/ethyl acetate (95:5), yielding 0.81 g of crystalline methyl (Z)-5-(2,5-dimethoxy-3,4,6-trimethylphenyl)-3-methyl-2-pentenoate. M.P. 87.5°–89° C.

c3) A solution of 0.8 g (2.6 mmol) of methyl (Z)-5-(2,5-dimethoxy-3,4,6-trimethylphenyl)-3-methyl-2-pentenoate in toluene (5 ml) was treated dropwise with 0.75 ml of a 3.5 molar Red-Al solution in toluene. After 2 hours at room temperature the mixture was poured into saturated ammonium chloride solution and extracted with ether. The combined extracts were washed with water, dried and concentrated to a colourless oil which was purified on silica gel with hexane/ethyl acetate 9:1→6:1, yielding 0.39 g of crystalline (Z)-5-(2,5-dimethoxy-3,4,6-trimethylphenyl)-3-methyl-2-penten-1-ol. M.P. 58.5°–60° C.

d3) Acetic anhydride (0.2 ml) was dissolved at 0° C. in pyridine (10 ml) together with (Z)-5-(2,5-dimethoxy-3,4,6-trimethylphenyl)-3-methyl-2-penten-1-ol (0.39 g; 1.4 mmol). A spatula tip of 4-dimethylaminopyridine was added and the reaction mixture was left at 0° C. for 20 minutes. Thereafter, the mixture was poured into 150 ml of ice-cold 2N hydrochloric acid and extracted with ether. The extracts were washed with water, dried briefly and freed from solvent, yielding 0.39 g of (Z)-5-(2,5-dimethoxy-3,4,6-trimethylphenyl)-3-methyl-2-pentenyl acetate as an almost colourless oil.

e3) A solution of (Z)-5-(2,5-dimethoxy-3,4,6-trimethylphenyl)-3-methyl-2-pentenyl acetate (0.98 g) in acetonitrile (15 ml) was treated dropwise at −20° C. with a solution of ceric ammonium nitrate (4.1 g) in water (15 ml). After 15 minutes the mixture was warmed to −10° C and left at this temperature for 1 hour. The mixture was diluted with ice-water and extracted twice with methylene chloride. The extracts were washed with water, dried and chromatographed on silica gel with hexane/ethyl acetate 95:5, yielding 0.67 g of (Z)-3-methyl-5-(2,4,5-trimethyl-3,6-dioxo-1,4-cyclohexadienyl)-2-pentenyl acetate as a pale yellow oil.

f3) A solution of 0.67 g (2.3 mmol) of (Z)-3-methyl-5-(2,4,5-trimethyl-3,6-dioxo-1,4-cyclohexadienyl)-2-pentenyl acetate in 20 ml of THF was treated dropwise with 8.1 ml of a 0.5M aqueous sodium dithionite solution. After completion of the addition the mixture was diluted with water and extracted three times with chloroform. The combined extracts were washed with water and freed from solvent. The residue was triturated in hexane yielding 0.57 g of (Z)-5-(2,5-dihydroxy-3,4,6-trimethylphenyl)-3-methyl-2-pentenyl acetate as a slightly coloured powder. M.P. 116.5°–117.5° C.

E. CATALYSTS

EXAMPLE 6

1) A solution of (R)-6,6'-dimethyl-2,2'-bis(diphenylphosphino)-1,1'-biphenyl (0.22 g; 0.4 mmol) and π-allylpalladium chloride dimer (74 mg; 0.2 mmol) in methanol (1.5 ml) was treated dropwise, after 15 minutes, with a solution of lithium perchlorate (212 mg; 2 mmol) in methanol (1 ml). The resulting suspension was stirred at room temperature for a further 12 hours. Thereafter, it was diluted with chloroform, washed with water and dried over sodium sulphate. After filtration the solvent was removed on a rotary evaporator and the residue was recrystallized from acetone, yielding 280 mg of colourless [[(R)-6,6'-dimethyl-1,1'-biphenyl-2,2'-bis(diphenylphosphine)]-P,P'][(η-3)-2-propenyl]palladium perchlorate with an optical rotation of +261.5° (DMSO, c=0.4).

2) A solution of (R)-6,6'-dimethyl-2,2'-bis(diphenylphosphino)-1,1'-biphenyl (0.22 g; 0.4 mmol) and π-allylpalladium chloride dimer (74 mg; 0.2 mmol) in methanol (1 ml) was treated with 680 mg (2 mmol) of sodium tetraphenylborate. The resulting precipitate was filtered off under suction after 4 hours, washed with 5 ml of 50% aqueous methanol and dissolved in 10 ml of acetone. Filtration of the resulting solution through Celite and subsequent dilution with 200 ml of ether gave an almost colourless precipitate (284 mg) of [[(R)-6,6-dimethyl -1,1'-biphenyl-2,2'-bis(diphenylphosphine)]-P,P'][(η-3)-2-propenyl]palladium tetraphenylborate.

F. CYCLIZATIONS

EXAMPLE 7

Experiment 1

A solution of (E)-5-(2,5-dihydroxy-3,4,6-trimethylphenyl)-3-methyl-2-pentenyl acetate (125 mg; 0.43 mmol), (R)-6,6'-dimethyl-2,2'-bis(diphenylphosphino-1,1'-biphenyl (7 mg, 3%) and π-allylpalladium chloride dimer (2.3 mg, 1.5%) in tetrahydrofuran (2 ml) was held at 65° C. for 12 hours. After cooling the solvent was removed and the residue was purified on 3 g of silica gel with hexane/ethyl acetate (99:1). After crystallization from pentane there was obtained 81 mg of (S)-3,4-dihydro-2,5,7,8-tetramethyl-2-vinyl-2H-[1]-benzopyran-6-ol. O.P. 53%.

Experiment 2

A solution of 125 mg (0.43 mmol) of (Z)-5-(2,5-dihydroxy-3,4,6-trimethylphenyl)-3-methyl-2-pentenyl acetate, 8 mg (3%) of (S)-2,2'-bis-(diphenylphosphino)-1,1'-binaphthalene and 2.3 mg (1.5%) of π-allylpalladium chloride dimer in DMSO (3 ml) was left at 60° C. for 17 hours. After cooling the mixture was diluted with water and extracted with ether. The extracts were washed with water, dried, concentrated and the residue was purified as in Experiment 1, yielding 86 mg of (S)-3,4-dihydro-2,5,7,8-tetramethyl-2-vinyl-2H-[1]-benzopyran-6-ol. O.P. 36%.

Experiment 3

A solution of 92 mg (0.3 mmol) of (E)-5-(3,6-dihydroxy-2,4,5-trimethylphenyl)-2-pentenyl methylcarbonate, 5 mg (3%) of (R)-6,6'-dimethyl-2,2'-bis(diphenylphosphino)-1,1'-biphenyl and 1.7 mg (1.5%) of π-allylpalladium chloride dimer in 2 ml of toluene was heated to 60° for 20 hours. After cooling the solvent was removed and the residue was purified as described in Experiment 1, yielding 54 mg of (S)-3,4-dihydro-2,5,7,8-tetramethyl-2-vinyl-2H-[1]benzopyran-6-ol. O.P. 20%.

Experiment 4

A solution of 106 mg (0.3 mmol) of (E)-5-(2,5-dihydroxy-3,4,6-trimethylphenyl)-3-methyl-2-pentenyl benzoate, 5 mg (3%) of (R)-6,6'-dimethyl-2,2'-bis-(diphenylphosphino)-1,1'-biphenyl and 1.7 mg (1.5%) of π-allylpalladium chloride dimer in 5 ml of THF was heated to 70° C. for 24 hours. After cooling the solvent was removed and the residue was Purified as described in Experiment 1, yielding 39 mg of (S)-3,4-dihydro-2,5,7,8-tetramethyl-2-vinyl-2H-[1]-benzopyran-6-ol. O.P. 56%.

Experiment 5

A solution of 106 mg (0.36 mmol) of (E)-5-(2,5-dihydroxy-3,4,6-trimethylphenyl)-3-methyl-2-pentenyl acetate and 9 mg (3%) of [[(R)-6,6'-dimethyl-1,1'-biphenyl-2,2'-bis(diphenylphosphine)]-P,P'][(η-3)-2-propenyl]-palladium perchlorate in 2 ml of DMSO was treated with 15 mg of calcium hydride and stirred at room temperature for three days. Thereafter, the mixture was poured into saturated ammonium chloride solution and extracted with ether. The combined extracts were washed with water and dried. The residue remaining after removal of the solvent was purified as described in Experiment 1, yielding 56 mg of (S)-3,4-dihydro-2,5,7,8-tetramethyl-2-vinyl-2H-[1]-benzopyran-6-ol. O.P. 33%.

Experiment 6

A solution of 104 mg (0.36 mmol) of (E)-5-(2,5-dihydroxy-3,4,6-trimethylphenyl)-3-methyl-2-pentenyl acetate, 11 mg (3%) of [[(R)-6,6'-dimethyl-1,1'-biphenyl-2,2'-bis(diphenylphosphine)]-P,P']-[(η-3)-2-propenyl]-palladium tetraphenylborate and 100 mg of 4-dimethylaminopyridine in 2 ml of DMSO was heated to 60° for 20 hours. After cooling the mixture was worked-up and chromatographed as described in Experiment 2, 63 mg of (S)-3,4-dihydro-2,5,7,8-tetramethyl-2-vinyl-2H-[1]-benzopyran-6-ol. O.P. 53%.

We claim:

1. A process for the manufacture of vinylchromanes having the formula

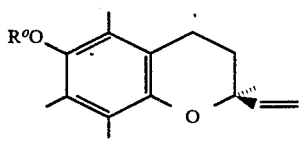

I wherein $R^o$ represents hydrogen or a cleavable protecting group,
which process comprises cyclizing a compound of the formula

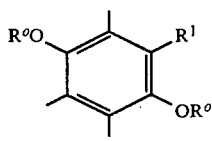

II wherein $R^o$ is defined above and $R^1$ is the residue —$CH_2CH_2$—$C(W)(CH_3)$—$CH=CH_2$ or —$CH_2$—$CH_2$—$C(CH_3)=CH$—$CH_2W$ where W is a leaving group,
by means of a chiral rhodium- or palladium-diphosphine complex.

2. A process according to claim 1, wherein said chiral rhodium-diphosphine complex is a compound having the formula $$[Rh(X)(Y)(L_{0,1, \text{ or } 2})]_{1 \text{ or } 2}$$  III wherein X is halide, $BF_6^-$, $PF_4^-$, or a residue of the formula Z—COO, which is optionally fixed to a carrier; Z is

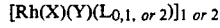

wherein $R^2$, $R^3$ and $R^4$ are halogen; $R^5$, $R^6$ and $R^7$ are H or lower alkyl; Y is chiral diphosphine ligand; and L is neutral ligand.

3. A process according to claim 2, wherein X is Z—COO$^-$ and Z is —$C(R^2R^3R^4)$.

4. A process according to claim 1, wherein said chiral palladium-diphosphine complex is a compound having the formula $$[Pd(X)(X^1)(Y)]$$  IV wherein X is halide, $ClO_4^-$ or $B(C_6H_5)_4^-$, which is optionally fixed to a carrier; $X^1$ is a η-allylic ligand having the formula

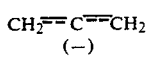

and Y is a chiral diphosphine ligand.

5. A process according to claim 2, wherein the chiral diphosphine ligand has the formula

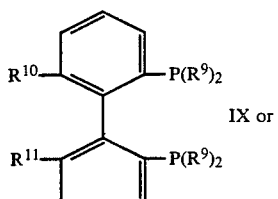

IX or

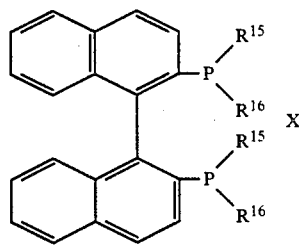

X wherein $R^9$ is phenyl which can optionally have in the meta- or para-position lower alkyl; each of $R^{10}$ and $R^{11}$ are $CH_3$ or $OCH_3$; each of $R^{15}$ and $R^{16}$ are phenyl which can optionally have in the meta- or para-position lower alkyl.

6. A process according to claim 4, wherein the chiral diphosphine ligand has the formula

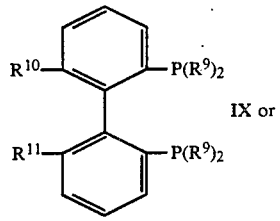

IX or

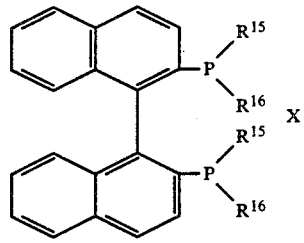

X wherein $R^9$ is phenyl which can optionally have in the meta- or para-position lower alkyl; each of $R^{10}$ and $R^{11}$ are $CH_3$ or $OCH_3$; each of $R^{15}$ and $R^{16}$ are phenyl which can optionally have in the meta- or para-position lower alkyl.

7. A process according to claim 1, wherein the complex is prepared in situ.

8. A process according to claim 1, wherein R⁰ represents methyl, acetyl or substituted benzyl.

9. A process according to claims 1, wherein W is an ester, a halide or an aryloxy group.

10. A process according to claim 9, wherein W is an ester.

11. A process according to claim 1, wherein the cyclization is carried out at a temperature of from about −20° C. to about 100° C.

12. A process according to claim 11, wherein the cyclization is carried and at a temperature of from about 0° C. to about 60° C.

13. A process according to claim 1, wherein the cyclization is carried out in a solvent selected from the group consisting of an aliphatic or aromatic hydrocarbon, a halogenated aliphatic or aromatic hydrocarbon, a cyclic ether, an ester, an alkanol, dimethylformamide, dimethyl sulphoxide and pyridine.

14. A process according to claim 1, wherein the cyclization is carried out in the presence of a base.

15. A process according to claim 14, wherein said base is an organic base.

16. A process according to claim 1, wherein the complex is used in an amount of from about 0.01 to about 10 wt.% based on Compound II.

17. A Process according to claim 16, wherein the complex is used in an amount of from about 1 to about 5 wt % based on Compound II.

18. A process according to claim 1. wherein the compound of formula I obtained is converted by hydroboration and oxidation into a compound having the formula

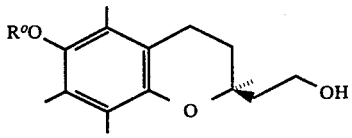

VI wherein R⁰ is hydrogen or a cleavable protecting group.

19. A process according to claim 18, wherein the compound of formula VI is converted into (R,R,R)-α-tocopherol.

* * * * *